United States Patent [19]

Rodewald

[11] 4,145,315
[45] Mar. 20, 1979

[54] SILICA-MODIFIED ZEOLITE CATALYST

[75] Inventor: Paul G. Rodewald, Rocky Hill, N.J.

[73] Assignee: Mobil Oil Corporation, New York, N.Y.

[21] Appl. No.: 862,461

[22] Filed: Dec. 20, 1977

Related U.S. Application Data

[60] Division of Ser. No. 753,748, Dec. 23, 1976, Pat. No. 4,100,219, which is a continuation-in-part of Ser. No. 672,194, Mar. 31, 1976, Pat. No. 4,060,568.

[51] Int. Cl.$^2$ ............................................. B01J 29/06
[52] U.S. Cl. ................................................. 252/455 Z
[58] Field of Search ...................................... 252/455 Z

[56] References Cited

U.S. PATENT DOCUMENTS

| 3,658,696 | 4/1972 | Shirely et al. | 252/455 Z |
| 3,980,586 | 9/1976 | Mitchell | 252/455 Z |

Primary Examiner—Carl Dees
Attorney, Agent, or Firm—Charles A. Huggett; Raymond W. Barclay

[57] ABSTRACT

A catalyst is provided, which is especially applicable for the selective production of $C_2$–$C_3$ olefins, comprising a crystalline aluminosilicate zeolite having a silica to alumina ratio of at least about 12, a constraint index, as hereinafter defined, within the approximate range of 1 to 12 and having contained within the interior crystalline structure thereof added amorphous silica in an amount of at least about 0.3 and preferably between about 0.5 and about 30 weight percent. The resultant catalyst is characterized by a n-hexane sorption capacity at a temperature of 90° C. and a n-hexane partial pressure of 83 mm. of mercury which is at least 1 percent less than corresponding sorption capacity under identical conditions for the unmodified zeolite. Generally, the n-hexane sorption capacity for the described silica-modified zeolite, at the above specified conditions, is 5 to 60 percent less than that for the zeolite which has not undergone treatment to incorpoate amorphous silica therein. The invention described herein also encompasses synthesis of the specified catalyst and use of the same in selectively converting lower monohydric alcohols and their ethers, especially methanol and dimethyl ether, to a hydrocarbon mixture rich in ethylene and propylene.

11 Claims, No Drawings

SILICA-MODIFIED ZEOLITE CATALYST

CROSS-REFERENCE TO RELATED APPLICATIONS

This application is a division of application Ser. No. 753,748, filed Dec. 23, 1976 U.S. Pat. No. 4,100,219 which in turn is a continuation-in-part of application Ser. No. 672,194, filed Mar. 31, 1976 and issued as U.S. Pat. No. 4,060,568 on Nov. 29, 1977.

BACKGROUND OF THE INVENTION

1. Field of the Invention

This invention relates to a crystalline alumino-silicate catalyst having added silica contained within its interior structure, the manufacture of such catalyst and use thereof in the selective conversion of low molecular weight monohydric alcohols or ethers to light olefins.

2. Description of the Prior Art

U.S. Pat. No. 2,722,504 describes a catalyst of an activated oxide such as silica gel having a thin layer of an organosilicone polymer deposited thereon to increase the organophilic character of the contact surface and, as such, seeks to avoid silica deposition.

Crystalline aluminosilicate zeolites, modified by reaction with an organic substituted silane, have been described in U.S. Pat. No. 3,682,996 to Kerr and in U.S. Pat. No. 3,698,157 to Allen et al. The former of these patents describes, as novel compositions of matter, crystalline aluminosilicate esters made by reacting a crystalline aluminosilicate having an available hydrogen atom with an organic silane having a SiH group. The resulting compositions were disclosed as being catalysts useful for hydrocarbon processes, particularly hydrocracking. In the latter of the above patents, the use of ZSM-5 type crystalline aluminosilicate zeolites, modified by treatment with an organic-radical substituted silane are described, together with the use of such modified zeolites in chromotographic separation of the compounds contained in a $C_8$ aromatic feed stock.

While the above-noted prior art is considered of interest in connection with the subject matter of the present invention, the catalyst, its manufacture and use in selectively producing low molecular weight olefins described herein has not, insofar as is known, been heretofore disclosed.

Low molecular weight olefins, i.e., ethylene and propylene, produced in accordance with the process described herein are valuable hydrocarbons and constitute building blocks from which many other commercially useful products can be manufactured.

SUMMARY OF THE INVENTION

In accordance with the present invention, there has been discovered a catalyst which is particularly applicable for selectively producing low molecular weight olefins from low molecular weight alcohols and/or ethers.

The catalyst of the invention comprises a crystalline aluminosilicate zeolite having a silica to alumina ratio of at least about 12, a constraint index within the approximate range of 1 to 12 and containing within the interior crystalline structure of said zeolite, amorphous silica added to the crystalline zeolite subsequent to the latter's formation in an amount of at least about 0.3 weight percent and generally in the approximate range of 0.5 to 30 weight percent. The resulting catalyst has a sorption capacity, as determined by n-hexane sorption at 90° C. and a partial pressure of 83 mm. of mercury, which is at least 1 percent and generally 5 to 60 percent less than that of the unmodified zeolite.

It has been found that such catalyst is suitably prepared by sorption of a silicon-containing compound into the pores of a crystalline aluminosilicate zeolite having the above-specified silica/alumina ratio and constraint index characteristics. The molecular dimensions of the silicon compound employed are such that it is readily sorbed into the pores of the crystalline aluminosilicate zeolite having the above-specified silica/alumina ratio and constraint index characteristics. The sorbed silicon compound contained in the pores of the crystalline aluminosilicate is subjected to calcination in an oxygen-containing atmosphere, such as air at a temperature in excess of about 300° C. but below a temperature at which crystallinity of the zeolite is adversely affected, generally between about 300° C. and about 700° C. to yield amorphous silica within the pores of the crystalline aluminosilicate zeolite.

The catalyst, so produced, is highly effective in converting low molecular weight alcohols or ethers derived therefrom, to an olefin rich hydrocarbon product. Thus, utilizing methanol as the feed, a representative hydrocarbon product composition is 50–75 percent olefins, 15–30 percent aromatics and remainder paraffins. Ethylene and propylene constitute approximately 75 percent of the olefin product with an ethylene/propylene ratio of greater than one. The xylene fraction of the aromatics produced is enriched in para-xylene very substantially over the normal equilibrium concentration of 24 weight percent.

Reaction conditions for carrying out the above specified selective conversions include a temperature between about 250° and about 600° C., a pressure between about 0.2 and about 30 atmospheres utilizing a feed liquid hourly space velocity (LHSV) between about 0.1 and about 50. The latter LHSV is based upon the volume of catalyst composition, i.e., total volume of active catalyst and binder therefor. The effluent is separated to remove the desired products, e.g., ethylene, propylene and paraxylene and unreacted material may be recycled for further reaction.

DESCRIPTION OF SPECIFIC EMBODIMENTS

The catalytic composition of this invention comprises a crystalline aluminosilicate zeolite characterized by a silica to alumina ratio of at least about 12, preferably in excess of 30, and a constraint index within the approximate range of 1 to 12. This zeolite has contained within the interior crystalline structure thereof added amorphous silica in an amount of at least 0.3 weight percent as a result of sorbing a silicon-containing compound into the pores of the zeolite and calcining.

The zeolites herein described are members of a novel class of zeolites exhibiting some unusual properties. These zeolites induce profound transformations of aliphatic hydrocarbons to aromatic hydrocarbons in commercially desirable yields and are generally highly effective in conversion reactions involving aromatic hydrocarbons. Although they have unusually low alumina contents, i.e., high silica to alumina ratios, they are very active even when the silica to alumina ratio exceeds 30. This activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g., of the X and A type. Furthermore, carbonaceous deposits, when formed, may be removed by burning at higher than usual temperatures to restore activity. In many environments, the zeolites of this class exhibit very low coke forming capability, conducive to very long times on stream between burning regenerations.

An important characteristic of the crystal structure of this class of zeolites is that is provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Likewise, this ratio excludes silica added in accordance with the present invention, to the crystalline aluminosilicate zeolite after its formation. Although catalysts with a silica to alumina ratio of at least 12 are useful, it is preferred to use catalysts having higher ratios of at least about 30. Such catalyst, after activation, acquire an intracrystalline sorption capacity for normal hexane which is greater than that for water, i.e., they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a small sample, approximately 1 gram or less, of zeolite at atmospheric pressure according to the following procedure. A sample of the zeolite in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical catalysts are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.5 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F. to 950° F., the constraint index will have a value for any given zeolite of interest herein within the approximate range of 1 to 12.

The class of zeolites defined herein is exemplified by ZSM-5, ZSM-11, ZSM-12, ZSM-35, ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in U.S. application Ser. No. 528,060, filed Nov. 29, 1974. This zeolite can be identified, in terms of mole ratios of oxides and in the anhydrous state, as follows:

$$(0.3-2.5)R_2O:(0-0.8)M_2O:Al_2O_3:8 \text{ } SiO_2$$

wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

$$(0.4-2.5)(R_2O:(0-0.6)M_2O:Al_2O_3:xSiO_2$$

wherein R is an organic nitrogen-containing cation derived from a 2-(hydroxyalkyl) trialkylammonium compound, wherein alkyl is methyl, ethyl or a combination thereof, M is an alkali metal, especially sodium, and x is from greater than 8 to about 50.

The synthetic ZSM-38 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33A.

TABLE I

| d(A) | $I/I_o$ |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-38 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-38 (after calcination at 600° C.) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| $\frac{R+}{R+ + M+}$ | 0.2-1.0 | 0.3-0.9 |
| $OH^-/SiO_2$ | 0.05-0.5 | 0.07-0.49 |
| $H_2O/OH^-$ | 41-500 | 100-250 |
| $SiO_2/Al_2O_3$ | 8.8-200 | 12-60 | wherein R is an organic nitrogen-containing cation derived from a 2-(hydroxyalkyl) trialkylammonium compound and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g., at 230° F. for from about 8 to 24 hours.

ZSM-35 is more particularly described in U.S. application Ser. No. 528,061, filed Nov. 29, 1974. This zeolite can be identified, in terms of mole ratios of oxides and in the anhydrous state, as follows:

$$(0.3-2.5)R_2O:(0-0.8)M_2O:Al_2O_3:8 \text{ } SiO_2$$

wherein R is an organic nitrogen-containing cation derived from ethylenediamine or pyrrolidine and M is an alkali metal cation, and is characterized by a specified X-ray powder diffraction pattern.

In a preferred synthesized form, the zeolite has formula, in terms of mole ratios of oxides and in the anhydrous state, as follows:

$$(0.4-2.5)R_2O:(0-0.6) M_2O:Al_2O_3:xSiO_2$$

wherein R is an organic nitrogen-containing cation derived from ethylenediamine or pyrrolidine, M is an alkali metal, especially sodium, and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3-11.5A. This very weak line, however, is determined not to be a significant line for ZSM-35.

TABLE II

| d(A) | $I/I_o$ |
|---|---|
| 9.6 ± 0.20 | Very Strong–Very Very Strong |
| 7.10 ± 0.15 | Medium |
| 6.98 ± 0.14 | Medium |

TABLE II-continued

| d(A) | I/I$_0$ |
|---|---|
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ratio n-hexane/2-methylpentane for ZSM-35 (after calcination at 600° C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH$^-$/SiO | 0.05–0.5 | 0.07–0.49 |
| H$_2$O/OH$^-$ | 41–500 | 100–250 |
| SiO$_2$/Al$_2$O$_3$ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of OH$^-$ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g., at 230° F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1000° F. for 1 hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35, with ZSM-5 particularly preferred.

The catalysts of this invention may be in the hydrogen form or they may be base exchanged or impregnated to contain ammonium or a metal cation complement. It is desirable to calcine the catalyst after base exchange. The metal cations that may be present include any of the cations of the metals of Groups I through VIII of the Periodic Table. However, in the case of Group IA metals, the cation content should in no case be so large as to effectively inactivate the catalyst.

In a preferred aspect of this invention, the catalysts hereof are selected as those having a crystal framework desnity, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erinonite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table including, by way of example, nickel, zinc, calcium or rare earth metals.

The crystals of zeolite in a form substantially free of alkali metal, i.e., containing less than about 1.5 weight percent alkali metal and preferably having at least a portion of the original cations associated therewith replaced by ammonium and/or hydrogen, are then contacted with a silicon-containing compound of molecular dimensions such that it is readily sorbed into the pores of the zeolite. Representative and preferred silicon-containing compounds include silicones of a molecular size capable of entering the pores of the zeolite. The silicone compound utilized is characterized by the general formula:

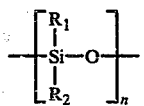

where $R_1$ and $R_2$ are individually selected from the group consisting of hydrogen, methyl, fluorine, chlorine and hydroxy and n is an integer of at least 3 and generally in the range of 4 to 1000. The molecular weight of the silicone compound employed is generally between about 250 and about 60,000 and preferably within the approximate range of 300 to 20,000. Representative silicone compounds include methylhydrogensilicone, dihydrogen silicone, dimethyl silicone, dichlorosilicone, fluorohydrogen silicone and difluorosilicone.

Silicone compounds are preferred as sources of silica in modification of the zeolite catalysts described herein since the zeolites so modified have been found to provide selective conversion of low molecular weight alcohols to light olefins with extremely low production of $C_9+$ hydrocarbons, e.g., durene. Another silicon-containing compound which may be employed is a silane having the following formula:

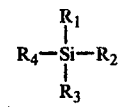

where $R_1$ and $R_2$ are hydrogen, fluorine, chlorine, methyl, ethyl, amino, methoxy or ethoxy; $R_3$ is hydrogen, fluorine, chlorine, methyl, amino or methoxy; and $R_4$ is hydrogen or fluorine. Other suitable silanes include poly-silanes, such as di-silanes, tri-silanes and higher silanes, up to deca-silanes. It is also contemplated to use derivatives of the aforenoted poly-silanes having methyl, chloro or fluoro substituents.

The silicon compound employed may be either in the form of a solution, a liquid or a gas under the conditions of contact with the zeolite. The pores of the latter are preferably, but not necessarily, saturated with the contacting media containing the silicon compound when a silicone compound is employed, it may be dissolved in a suitable solvent therefor, e.g., n-hexane, pentane, heptane, benzene, toluene, xylenes, trimethyl benzene, chloroform, carbon tetrachloride, dichloro benzene or trimethyl benzene. Contact between the silicone compound and the zeolite is maintained at a temperature between about 10° C. and about 200° C. for a period of time sufficient to sorb the ultimately desired amount of silicone therein. Time of contact will generally be within the range of 0.2 to 5 hours, during which time the mixture is desirably subjected to evaporation of the solvent fluid. The resulting residue is then calcined in an oxygen-containing atmosphere, preferably air, at a rate of 0.2° to 5° C./minute to a temperature greater than 300° C. but below a temperature at which the crystallinity of the zeolite is adversely affected. Generally, such temperature will be below 700° C. Preferably, the temperature of calcination is within the approximate range of 350° to 550° C. The product is maintained at the calcination temperature usually for 1 to 24 hours to yield a zeolite having silica contained in the interior porous structure thereof.

When the employed silicon compound is a silane, the latter desirably undergoes catalyzed hydrolysis, either by base catalyzed hydrolysis, e.g., by contacting the zeolite containing the sorbed silane with a solution of aqueous ammonia or by acid catalyzed hyrolysis in the presence of Lewis or Bronsted acids, such as for example, by contact with an aqueous solution of hydrochloric acid. Contact of the zeolite contained sorbed silane with a suitable acid or base is maintained for a period of time sufficient to effect the desired hydrolysis with evolution of hydrogen. The resulting product is then calcined as above described to yield a catalyst of the specified crystalline aluminosilicate zeolite having silica contained within its interior structure.

The amount of silica incorporated with the zeolite will depend on several factors. One of these is the time that the zeolite and the silicon-containing source are maintained in contact with each other. With greater contact times, all other factors being equal, a greater amount of silica is incorporated with the zeolite. Other factors upon which the amount of silica incorporated with the zeolite is dependent include temperature, concentration of the treating compound in the contacting media, the degree to which the zeolite has been dried prior to contact with the silicon-containing compound, the conditions of hydrolysis, when practiced, and calcination of the zeolite after contact of the same with the treating compound and the amount and type of binder incorporated with the zeolite. Generally, the amount of silica contained in the interior porous structure of the zeolite will be between about 0.3 and about 40 and preferably between about 0.5 and about 30 weight percent.

The amount of silica incorporated into the zeolite crystal can be assessed from a reduction in the zeolitic sorption capacity. The latter is determined from the amount of n-hexane sorbed at a temperature of 90° C. and a n-hexane partial pressure of 83 mm. mecury and is determined from the increase in zeolite weight upon sorption. The decrease in sorption capacity of the zeolite under the above conditions attributable to the presence of added amorphous silica is at least 1 percent and generally in the range of 5 to 60 percent. Representative sorption data for a binder-free zeolite and an alumina-zeolite extrudate are shown below:

| Binder-Free ZSM-5 | Mg. n-hexane Sorbed Per Gram of ZSM-5 |
|---|---|
| No added amorphous silica | 105 |
| Intracrystalline amorphous silica (24%) | 55 |
| Extrudate-65% ZSM-5-35% $Al_2O_3$ | |
| No added amorphous silica | 80 |
| Intracrystalline amorphous silica (14%) | 61 |

In practicing the desired conversion process it may be desirable to incorporate the modified zeolite in another material resistant to the temperatures and other conditions employed in the conversion process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the modified zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the modified zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia. The matrix may be in the form of a cogel. The relative proportions of finely divided modified zeolite and inorganic oxide gel matrix may vary widely with the zeolite content ranging from between about 1 to about 99 percent by weight and more usually in the range of about 5 to about 80 percent by weight of the composite.

Alternatively, the zeolite may be modified, as described hereinabove, after being combined with the aforenoted matrix materials.

The process of this invention is conducted such that conversion is carried out in the vapor phase by contact in a reaction zone, such as, for example, a fixed bed of catalyst, under effective conversion conditions, said catalyst being characterized as above-described and preferably hydrogen exchanged such that a predominate portion of its exchangeable cations are hydrogen ions. In general, it is contemplated that more than 50 percent and preferably more than 75 percent of the cationic sites of the crystalline aluminosilicate zeolite, above-described, will be occupied by hydrogen ions.

The conversion process described herein may be carried out as a batch-type, semi-continuous or continuous operation utilizing a fixed or moving bed catalyst zone wherein the charge is passed concurrently or countercurrently through a moving fluidized bed of the catalyst. The fluidized catalyst after use is conducted to a regeneration zone wherein coke is burned from the catalyst in an oxygen-containing atmosphere, e.g., air, at an elevated temperature, after which the regeneration catalyst is recycled to the conversion zone for further contact with the charge.

The process of the invention involves the conversion of lower monohydric alcohols, having up to four carbon atoms, and their ethers, especially methanol and dimethyl ether, to a hydrocarbon mixture rich in $C_2$-$C_3$ olefins, by contact, under conversion conditions, with the above described catalyst. It has been found that such catalyst affords a substantially higher selectivity for ethylene production over corresponding use of zeolite which has not undergone modification by silica addition. It has further been found that with the catalysts described herein, only moderate amounts of durene are formed during the desired alcohol and/or ether conversion. As is well known, durene is an undesirable component in gasoline, tending to crystallize in the carburetor of an internal combustion engine causing the latter to stall. High durene make, usually associated with low operating temperatures during conversion of low molecular weight alcohols has not been observed using the catalysts described herein.

It is contemplated that any monohydric alcohol having from 1 to 4 carbon atoms or ethers derived from these alcohols may be used as feed to the process of this invention. Thus, methanol, ethanol, iso-propanol, n-butanol, sec-butanol, and isobutanol may be used either alone or in admixture with ethers derived from such alcohols. Likewise, the noted ethers, e.g., methyl-ethyl ether may be similarly used. Particularly preferred feeds are methanol, dimethyl ether and mixtures thereof.

It has further been found that the presence of water in the described alcohol and/or ether reaction feed serve to enhance the desired selective production of $C_2$-$C_3$ olefins. It is accordingly a preferred embodiment of this invention that the low molecular weight alcohol and/or ether feed contain water when contacted with the silica-modified crystalline aluminosilicate zeolite catalyst described herein. The amount of water present may be as high as 100 moles of water per mole of the alcohol and/or ether feed. Generally, the amount of water present, when this technique is employed, is between about 3 and about 30 mole of water per mole of the organic, i.e., alcohol and/or ether, charge.

The present process comprises conversion of such alcohols and/or ethers in the presence of the specified catalyst at a temperature between about 250° C. and about 600° C. and preferably between about 300° C. and about 500° C. at a pressure between about 0.2 and about 30 atmospheres utilizing a feed liquid hourly space velocity (LHSV) between about 0.1 and about 50. The latter is based upon the volume of catalyst composition, i.e., total volume of active catalyst and binder therefor. The effluent is separated and distilled to remove the desired products of light olefinic hydrocarbons and aromatics, such as para-xylene. Any unreacted material may be recycled for further reaction.

The following examples will serve to illustrate the catalyst and conversion process of the present invention without limiting the same:

EXAMPLE 1

Four (4.00) grams of an NH$_4$ZSM-5 extrudate of 1–2μ crystal size and containing 35 weight percent of alumina and 65 weight percent of the zeolite were contacted with 0.63 gram of methylhydrogensilicone dissolved in 40 cc. n-hexane. The mixture was evaporated over 30 minutes at 75° C. The resulting solid containing sorbed methylhydrogensilicone to yield a resulting composite of HZSM-5 and alumina containing amorphous silica within its interior porous structure.

The silica-modified HZSM-5 catalyst prepared as above was found to contain 13.6 weight percent silica distributed between the alumina binder and the zeolite. Sorption with n-hexane showed that silica occupied 13 percent of the zeolite pore volume. Steam stability of the silica-modified HZSM-5 was found to be substantially the same as the parent HZSM-5.

EXAMPLE 2

Methanol was passed over a sample of the catalyst of Example 1 at 320°–340° C. at a liquid hourly space velocity (LHSV) of 1–4. The catalyst showed good selectivity to ethylene of 20 to 30 percent over a range of conversion from 20 to 100 percent. The C$_9$+ content of the hydrocarbon product was typically 1–3 weight percent compared to approximately 10 weight percent for unmodified HZSM-5. The following table summarizes the hydrocarbon product distribution taken after 48 hours time on stream (340° C., LHSV = 1, 91% conversion).

The data in parentheses show the hydrocarbon product distribution obtained by passing methanol over the parent HZSM-5 under comparable experimental conditions (320° C., LHSV = 1, 91% conversion). The intracrystalline silica modification catalyst shows increased selectivity to ethylene and propylene as well as a considerably lowered selectivity to the undesirable C$_9$+ product. Durene has been reduced in order of magnitude from 4.3% to 0.4%. Also, the p-xylene content in the xylenes has been increased from 58% to 85%.

| Component | Wt. % | (Wt. %)$^a$ |
|---|---|---|
| Methane | 0.7 | (0.4) |
| Ethylene | 21.2 | (18.1) |
| Propane | 4.9 | (3.3) |
| Propylene | 12.5 | (8.6) |
| i-Butane | 6.0 | (5.3) |
| n-Butane | 2.0 | (1.4) |
| Butenes | 6.8 | (6.3) |
| C$_5$ - C$_6$ | 26.3 | (34.0) |
| Benzene | 1.2 | (—) |
| Toluene | 2.6 | (1.3) |
| Ethylbenzene | 0.4 | (0.1) |
| Xylenes | 7.1$^b$ | (4.2)$^c$ |
| C$_7$ - C$_8$ | 5.5 | (8.5) |
| C$_9$+ | 2.6$^d$ | (10.7)$^e$ |

$^a$Data obtained from parent HZSM-5.
$^b$Contains 85% p-xylene in xylene isomers.
$^c$Contains 58% p-xylene in xylene isomers.
$^d$Including 0.4% durene.
$^e$Including 4.3% durene.

EXAMPLE 3

4.00 gram of binder-free HZSM-5 of 1–2μ crystal size was contacted with 0.02 gram methylhydrogensilicone dissolved in 40 cc n-hexane. This mixture was then treated as in Example 1 to give silica-modified HZSM-5 containing 0.5% silica.

EXAMPLE 4

Methanol was passed over a sample of the catalyst of Example 3 at 320°–360° C. at a LHSV of 2.0. The catalyst showed 20–30% selectivity to ethylene over a range of conversion from 30 to 100%. The following table summarizes the hydrocarbon product distribution taken after 5 hours time on stream (340° C., LHSV = 2, 61% conversion).

| Component | Wt. % | Component | Wt. % |
|---|---|---|---|
| Methane | 0.4 | C$_5$ - C$_6$ | 16.3 |
| Ethylene | 26.1 | Benzene | 3.1 |
| Propane | 2.9 | Toluene | 2.8 |
| Propylene | 19.3 | Ethylbenzene | 0.3 |
| i-Butane | 3.4 | Xylenes | 5.8$^a$ |
| n-Butane | 1.0 | C$_7$ - C$_8$ | 4.3 |
| Butenes | 10.6 | C$_9$+ | 3.7$^b$ |

$^a$Contains 76% p-xylene in xylene isomers.
$^b$Including 1.1% durene.

EXAMPLE 5

4.00 gram of binder-free ZSM-5 of 1–2μ crystal size was contacted with 0.32 gram methylhydrogensilicone dissolved in 40 cc n-hexane. This mixture was then treated as in Example 1 to give silica-modified HZSM-5 containing 7.4% silica.

EXAMPLE 6

Methanol was passed over a sample of the catalyst of Example 5 at 370° C. at a LHSV of 1–4. The catalyst showed 20–32% selectivity to ethylene over a range of conversion from 15 to 100%. The following table summarizes the hydrocarbon product distribution taken after 24 hours time on stream (370° C., LHSV = 1.0, 82% conversion).

| Component | Wt. % | Component | Wt. % |
|---|---|---|---|
| Methane | 1.3 | C$_5$–C$_6$ | 16.0 |
| Ethylene | 26.2 | Benzene | — |
| Propane | 2.4 | Toluene | 2.2 |
| Propylene | 18.7 | Ethylbenzene | 0.5 |
| i-Butane | 4.4 | Xylenes | 6.2$^a$ |
| n-Butane | 1.0 | C$_7$–C$_8$ | 6.2 |
| Butenes | 10.8 | C$_9$+ | 4.4$^b$ |

$^a$Contains 81% p-xylene in xylene isomers.
$^b$Including 0.8% durene.

EXAMPLE 7

4.00 gram of binder-free HZSM-5 of 0.02–0.05μ crystal size was contacted with 1.30 gram methylhydrogensilicone dissolved in 40 cc n-hexane. This mixture was then treated as in Example 1 to give silica-modified HZSM-5 containing 24% silica.

EXAMPLE 8

Methanol was passed over a sample of the catalyst of Example 7 at 340° C. at a LHSV of 1–4. The catalyst showed 20–25% selectivity to ethylene over a range of conversion from 40 to 100%. The following table summarizes the hydrocarbon product distribution taken after 31 hours time on stream (340° C., LHSV = 3.0, 79% conversion).

The data in parentheses show the hydrocarbon product distribution obtained by passing methanol over the parent HZSM-5 at the same conversion level. The intracrystalline silica-modified catalyst shows increased selectivity to ethylene and propylene and a considerably lowered selectivity to the $C_9+$ product. Durene has been reduced from 18% to 0.7%.

| Component | Wt. % | (Wt. %)$^a$ |
|---|---|---|
| Methane | 0.5 | (0.6) |
| Ethane | — | (0.1) |
| Ethylene | 21.9 | (12.2) |
| Propane | 2.7 | (4.0) |
| Propylene | 15.2 | (5.7) |
| i-Butane | 3.7 | (2.3) |
| n-Butane | 1.0 | (1.6) |
| Butenes | 9.2 | (3.3) |
| $C_5 - C_6$ | 25.4 | (18.9) |
| Benzene | — | (3.6) |
| Toluene | 2.2 | (11.5) |
| Ethylbenzene | 0.4 | (2.3) |
| Xylenes | 8.2$^b$ | (3.6)$^c$ |
| $C_7 - C_8$ | 5.0 | (3.7) |
| $C_9+$ | 4.5$^d$ | (27.3)$^e$ |

$^a$Data obtained from parent HZSM-5.
$^b$Contains 75% p-xylene in xylene isomers.
$^c$Contains 31% p-xylene in xylene isomers.
$^d$Including 0.7% durene.
$^e$Including 18% durene.

EXAMPLE 9

A five gram sample of HZSM-5 of 0.02–0.05 micron crystal size was placed in a glass tube fitted with a fritted glass disc. Dimethylsilane was passed through the bed of HZSM-5 at a rate of 40 cc/minute. After 15 minutes, the HZSM-5 has sorbed 0.60 gram of dimethylsilane. The product was added to 200 cc of 15 percent aqueous ammonia to hydrolyze the silane. Hydrogen was evolved rapidly. After one hour, the product was filtered and calcined at 1° C./minute to 538° C. and held at this temperature for 6 hours.

The above procedure was repeated a total of three times to yield a silica-loaded HZSM-5 containing 5 weight percent of added silica.

EXAMPLE 10

Methanol was passed over 1 gram of the silica-modified HZSM-5 catalyst of Example 9 at a temperature of 300° C. utilizing a liquid hourly space velocity of 1.25. After 6.5 hours on stream, 29 percent of the charge was converted to give the following product distribution:

| Component | % | Component | % |
|---|---|---|---|
| Methane | 0.4 | Pentenes* | 8.8 |
| Ethylene | 20 | Hexenes* | 6.1 |
| Propane | 2.0 | Ethylbenzene | 2.4 |
| Propylene | 14 | Xylenes | 6.8 |
| iso-Butane | 5.1 | $C_9+$ | 23 |
| n-Butane | 0.5 | | |
| Butenes | 11 | | |

*Contains 2-3% paraffins

The xylene isomer distribution was 75% para-, 17% meta- and 8% orthoxylene.

EXAMPLE 11

Methanol (2.4 parts by weight) was contacted with 1.0 part by weight of 0.02–0.05 micron silica-modified HZSM-5 prepared as in Example 9 at a temperature of 320° C. and a liquid hourly space velocity of 1.0 for a 100 percent conversion of the methanol feed. Analysis of the resulting product showed an ethylene content of 14 weight percent. This value corresponds to a 75 percent increase in ethylene selectivity, i.e., from 8 to 14 percent, when compared to the parent HZSM-5 under comparable reaction conditions.

EXAMPLE 12

A water-methanol mixture (10 moles water to one mole methanol) was passed over the catalyst of Example 1 at 330°–360° C. and 1 weight hourly space velocity relative to methanol. The catalyst showed 30-35% selectivity to ethylene over a range of conversion of 10-90%. The following table summarizes the hydrocarbon product distribution at 30 hours time on stream (350° C., WHSV = 1.0, 54% conversion).

The data in parentheses show the hydrocarbon product distribution obtained by passing pure methanol over the above catalyst at the same conversion. The selectivity to ethylene has been significantly increased from 24 to 33% by the presence of water, while the $C_9+$ fraction has been reduced from 2.7 to 1.5%. Durene has been essentially eliminated. The xylene fraction contained 99% of the para-isomer.

| Component | Wt. % | (Wt. %)$^a$ |
|---|---|---|
| Methane | 0.5 | (0.8) |
| Ethylene | 32.6 | (23.6) |
| Propane | 2.3 | (2.7) |
| Propylene | 25.0 | (19.6) |
| i-Butane | 5.4 | (3.4) |
| n-Butane | 0.6 | (1.1) |
| Butenes | 4.2 | (6.9) |
| $C_5 - C_6$ | 10.5 | (15.0) |
| Benzene | — | — |
| Toluene | 1.5 | (3.1) |
| Ethylbenzene | 0.3 | (1.2) |
| Xylenes | 10.7$^b$ | (6.1)$^c$ |
| $C_7 - C_8$ | 1.1 | (9.3) |
| $C_9+$ | 1.5$^d$ | (2.7)$^e$ |

$^a$Data obtained using pure methanol.
$^b$Contains 99% p-xylene in xylene isomers.
$^c$Contains 74% p-xylene in xylene isomers.
$^d$Durene less than 0.1%.
$^e$Including 0.4% durene.

I claim:

1. A catalyst composition comprising a crystalline aluminosilicate zeolite having a silica to alumina ratio of at least about 12, a constraint index within the approximate range of 1 to 12 and containing within the interior crystalline structure thereof added amorphous silica in an amount of at least about 0.3 weight percent, introduced therein as a result of (1) contact with a silicone under conditions such that the silicone is sorbed into the pores of the crystalline aluminosilicate zeolite and (2) subsequent calcination, said catalyst being characterized by a n-hexane sorption capacity at a temperature of 90° C. and a n-hexane partial pressure of 83 mm. of mercury which is at least 1 percent less than the corresponding sorption capacity under identical conditions for the unmodified zeolite.

2. The catalyst composition of claim 1 wherein the amount of added amorphous silica is between about 0.5 and about 30 weight percent.

3. The catalyst composition of claim 1 wherein said crystalline aluminosilicate zeolite is ZSM-5.

4. The catalyst composition of claim 1 wherein said zeolite is ZSM-5 predominately in the hydrogen form.

5. A method for preparing a catalyst composition which comprises sorbing into the pores of a crystalline aluminosilicate zeolite, characterized by a silica to alumina ratio of at least about 12 and a constraint index within the approximate range of 1 to 12, a silicone of such molecular dimensions that it readily enters the pores of said zeolite, and calcining the resulting product in an oxygen-containing atmosphere at a temperature between about 300° and about 700° C. for 1 to 24 hours to yield a composite of said crystalline aluminosilicate zeolite having amorphous silica contained within its interior structure.

6. The method of claim 5 wherein said crystalline aluminosilicate zeolite is ZSM-5.

7. The method of claim 5 wherein said silicone is characterized by the general formula:

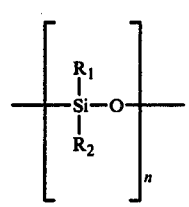

where $R_1$ and $R_2$ are individually selected from the group consisting of hydrogen, methyl, fluorine, chlorine and hydroxy and n is an integer of at least 3.

8. The method of claim 7 wherein n is an integer in the range of 4 to 1000.

9. The method of claim 7 wherein said silicone is methylhydrogen silicone.

10. The catalyst composition of claim 1 wherein said crystalline aluminosilicate zeolite having added amorphous silica is contained in a matrix.

11. The method of claim 5 wherein said temperature is within the approximate range of 350° to 550° C.

* * * * *